United States Patent [19]

Kurimoto

[11] Patent Number: 4,828,550
[45] Date of Patent: May 9, 1989

[54] ENTERAL FEEDING AND SUCTION TUBE ASSEMBLY

[75] Inventor: Munehito Kurimoto, Asabacho, Japan

[73] Assignee: Sherwood Medical Company, St. Louis, Mo.

[21] Appl. No.: 24,634

[22] Filed: Mar. 11, 1987

[30] Foreign Application Priority Data

Mar. 14, 1986 [JP]  Japan ................... 61-56656

[51] Int. Cl.⁴ ............................................. A61M 5/00
[52] U.S. Cl. ...................................... 604/171; 604/270
[58] Field of Search ............... 604/171, 172, 164–169, 604/280, 284, 43–45, 161, 54, 270, 173, 264, 39; 128/188

[56] References Cited

U.S. PATENT DOCUMENTS

| | | | |
|---|---|---|---|
| 3,144,868 | 10/1960 | Jascalevich | 604/43 |
| 3,155,097 | 11/1964 | Barron | 604/270 |
| 3,528,427 | 9/1970 | Sheridan | 604/45 |
| 4,167,939 | 9/1979 | Storz | 604/84 |
| 4,175,564 | 11/1979 | Kwak | 604/54 |
| 4,249,535 | 2/1981 | Hargest, III | 604/54 |
| 4,402,685 | 9/1983 | Buhler et al. | 604/280 |
| 4,468,216 | 8/1984 | Muto | 604/43 |
| 4,543,089 | 9/1985 | Moss | 604/43 |
| 4,613,323 | 9/1986 | Norton et al. | 604/270 |
| 4,661,110 | 4/1987 | Fortier et al. | 604/256 |
| 4,687,470 | 8/1987 | Okada | 604/171 |

FOREIGN PATENT DOCUMENTS

| | | | |
|---|---|---|---|
| 445218 | 4/1936 | United Kingdom | 128/188 |
| 2032780 | 5/1980 | United Kingdom | 604/43 |

Primary Examiner—John D. Yasko
Attorney, Agent, or Firm—Stanley N. Garber; Andrew J. Beck; Richard D. Allison

[57] ABSTRACT

A suction tube is adapted to receive an enteral feeding catheter through its lumen and has a longitudinally splittable wall to allow the suction tube to be removed from a patient while leaving the feeding catheter in place. In a modified embodiment, the suction tube has a second longitudinally extending lumen in the wall thereof which may be used for air bleed, sample aspiration and delivery of medication.

7 Claims, 1 Drawing Sheet

ENTERAL FEEDING AND SUCTION TUBE ASSEMBLY

BACKGROUND OF THE INVENTION

This invention relates to a suction tube for use with an enteral feeding catheter, and to an enteral feeding tube assembly.

Enteral eeding is the medical procedure whereby food is delivered directly to the intestine following, for example, a stomach operation. Liquid nutrients are usually supplied through a catheter inserted into the intestine through the patient's nose and alimentary canal. A suction tube is often necessary to remove unwanted liquids and gases from the region of the operation.

The feeding catheter and suction tube may be separately inserted, one through each nostril, but this has the disadvantage that both nostrils are blocked, which is painful to the patient.

An alternative 'duplex' construction is disclosed in Japanese Patent Publication No. 222067/1985 in which a single tube has feeding and suction lumens.

An enteral feeding catheter normally has a relatively small diameter compared with the suction tube. Following an operation the suction tube can usually be removed after several days whereas the feeding catheter may remain in-situ for a comparatively long period. The 'duplex' type feeding tube has the disadvantage that although only one nostril is blocked, the patient must endure pain from the relatively large bore suction tube long after the need for suction has passed.

SUMMARY OF THE INVENTION

It is an object of the present invention to provide a feeding catheter and suction tube set in which the suction tube may be more easily removable from within the patient when suctioning is unnecessary. One possible solution would be to mount an auxiliary tube inside a prior art suction tube, the suction can only be removed while leaving the auxliary tube in place, by sliding the suction tube along the auxiliary tube out of the patient's nose. In such a case, the auxiliary tube, or catheter, would have to be at least twice the length of suction tube to accommodate the suction tube outside the patient. Friction would also make it difficult to slide the suction tube along the catheter to a position wholly outside the patient. Furthermore, such a long feeding catheter would restrict the flow rate of food in comparison to a catheter of standard length.

Finally, such excessive feeding catheter length would be awkward to secure to the patient or to other apparatus.

According to the invention there is provided a suction tube having a lumen, a proximal end adapted for connection to a source of suction and a distal end having openings therein and an enteral feeding catheter slidably extending within the lumen of the suction tube. The suction tube incorporates at least two weakened, linear portion in the wall thereof, extending the length of the suction tube which, in use, facilitates longitudinal splitting of the tube.

Such a suction tube has the advantage that it can accommodate a feeding tube in the bore thereof, so having the advantages of a 'duplex' tube, and yet is removable from the patient. without requiring an excessively long feeding catheter. The feeding catheter is of the usual length and has openings at a distal end for discharge of feeding liquid.

In a first preferred embodiment, the suction tube has two linear weakened portions extending longitudinally the length of the suction tube, making the suction tube splittable into two sections, one each to be gripped in the practitioner's hands and pulled apart for removal. Alternately, a single line or weakened portion may be provided.

In an alternative embodiment of the invention, the suction tube has a longitudinally extending lumen in the wall thereof, separate from the main suction lumen through which the feeding catheter extends, which can be used to relieve excess suction in the alimentary canal and to provide an air bleed. The lumenmay also be used to aspirate a sample from the distal end of the suction tube or to pass medication to the alimentary canal.

The suction tube may have a connector at the proximal end thereof which has an opening to receive an enteral feeding catheter in sliding sealing engagement, and a branch pipe for connection to a suction source.

The invention also provides an enteral feeding tube set comprising a suction tube as aforesaid and an enteral feeding tube.

BRIEF DESCRIPTION OF THE DRAWINGS

Other features of the invention will be apparent from the following description of the two preferred embodiments shown by way of example only in the accompanying drawings briefly described hereafter.

With reference to FIG. 1, there is shown a first embodiment according to the invention including an enteral feeding catheter 11 having the usual proximal connection 12, feeding eyes 13 and weighted tip 14. The catheter 11 passes through a suction tube 16 which has a plurality of suction holes 17 at the distal end thereof.

Figure 1:
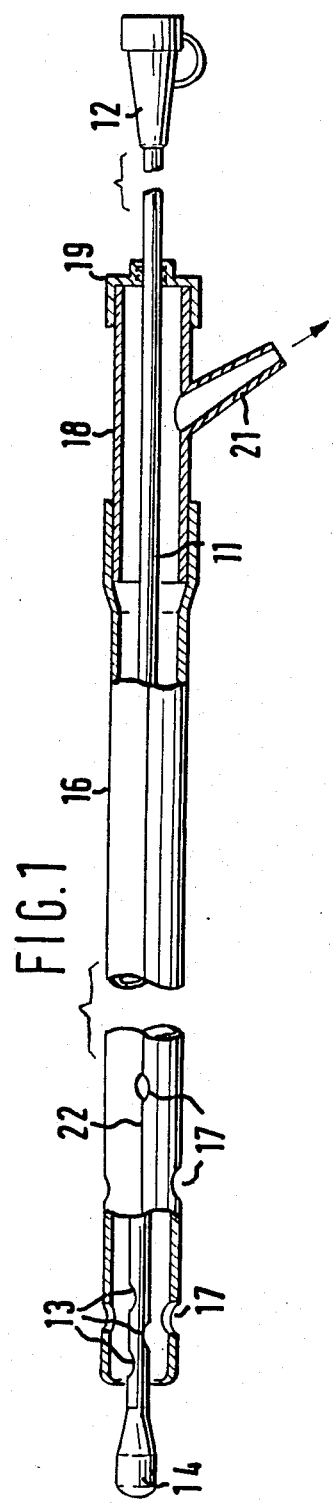
FIG. 1 is a side view of a first embodiment of a feeding and suction tube set according to the invention.

The feeding catheter and suction tube are made of materials which will not be deteriorated by intenstinal juices but which are sufficiently flexible to pass easily through the nose and the alimentary canal. Suitable materials are PVC and polyethylene. The inner surface of suction tube 16 has a matte or roughened finish to promote free sliding along the feeding catheter 11. The suction tube 16 preferably has higher rigidity and elasticity than the feeding catheter. The distal end of the suction tube is open but rounded as shown to avoid damage to body tissue.

A connector 18 is inserted into the proximal end of the suction tube and is closed about the feeding catheter by a cap 19. The connector 18 has a branch pipe 21 for connection to a suction source. The tube 16, connector 18 and cap 19 are secured together sufficient to resist suction applied to the branch pipe 21; the parts may be in sealing frictional engagement for example.

The suction tube includes two longitudinally extending linear weakened portions or lines 22 (FIG. 3) which extend from the proximal to distal end. The weakened lines 22 may be formed of a filler material which is the same as the suction tube, or which also includes other materials, which bonds sufficiently strongly to the suction tube wall to permit insertion and use of the tube but which separates freely with the fingers to allow the suction tube to be removed from the feeding tube. Alternatively, the filler material may be mixed with the suction tube so as to give free splitting in a longitudinal direction.

The feeding catheter and/or suction tube may be provided with depth graduation marks to allow the insertion length of the catheter to be adjusted relative to the suction tube.

In use, the relative lengths of tube 16 and catheter 11 are adjusted and the assembly inserted through one nostril of the patient and through the alimentary canal to the stomach region. The catheter and tube are connected to respective food and suction sources and used in a conventional manner. One nostril of the patient is free to provide an airway.

When the need for suction has passed the branch connector 8 is disconnected from the suction tube, and the proximal end of the suction tube is split; the user holds one half of the tube in each hand and pulls the tube out of the patient, splitting the tube as it is removed.

Figure 2:
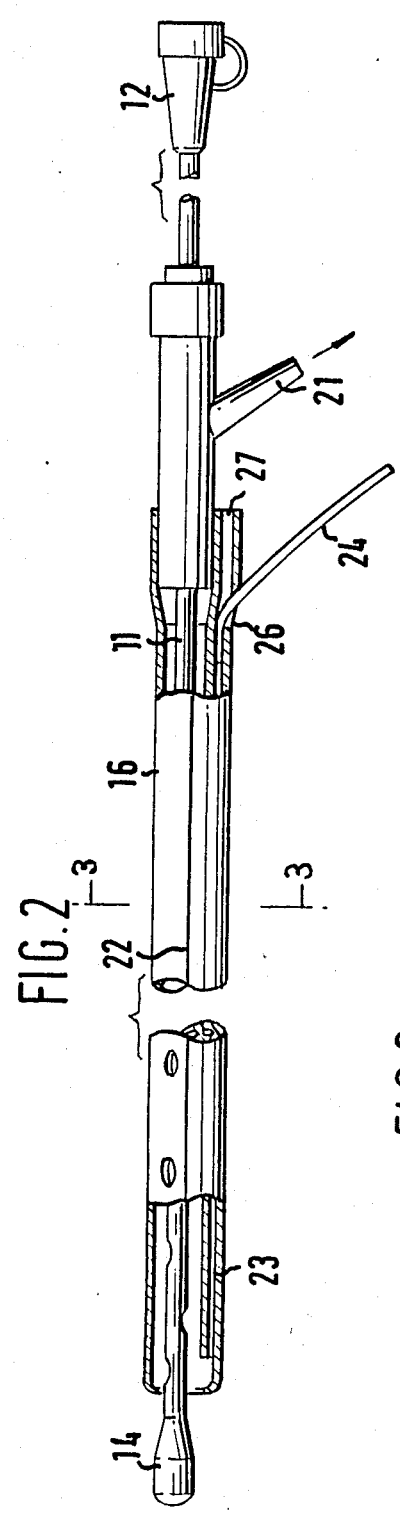
FIG. 2 is a side view of a second emodiment of a catheter suction tube set according to this invention.
Figure 3:
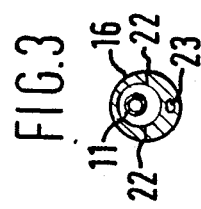
FIG. 3 is a section view of the set shown in FIG. 2, taken substantially along line 3—3 of FIG. 2.

A modification of the feeding tube assembly is shown in FIGS. 2 and 3, which carries corresponding reference numerals. The suction tube includes a lumen 23 in the wall thereof which is open to the interior of the suction tube at the distal end and has a radial opening 26 and an axial opening 27 at the proximal end. A removable tube 24 maybe inserted through the radial opening 26 as shown.

The lumen 23 has several uses. When the tube 24 is removed it may act as a vent to relieve suction in the alimentary canal and thereby avoid damage to the mucosa which may occur if the wall of the alimentary canal is sucked against the suction tube.

When the tube 24 is in place, the axial opening 27 of the lumen 23 is blocked. In this condition, the tube 24 may be used to aspirate a sample from the distal end o the suction tube or alternatively to irrigate the alimentary canal. The tube 24 may also be used to administer a medicinal preparation.

Other variations are possible and it is intended that the invention be limited only by the scope of the claims appended hereto.

What is claimed is:

1. An enteral feeding and suction tube assembly for insertion into the nasal gastric passageway of a patient, the assembly comprising an enteral feeding catheter having a lumen extending therethrough between proximal and distal ends, a means at the proximal end thereof for connecting the lumen to a source of feeding liquid, and holes at said distal end thereof for discharging said feeding liquid from said lumen; a suction tube having proximal and distal ends for substantially encasing said catheter and having a lumen substantially larger than and generally spaced apart from the lumen of the catheter, said catheter extending from the proximal end to the distal end of said suction tube, a connection means at said proximal end of said suction tube for connecting the lumen of said suction tube to a source of suction, suction openings in said distal end of said suction tube, and said suction tube including a means for longitudinally splitting and removing said suction tube from said catheter.

2. An assembly according to claim 1, wherein said means for longitudinally splitting is in the form of two parallel linear weakened portions of said suction tube extending the length thereof.

3. An assembly according to claim 1 wherein a second longitudinally extending lumen is provided in a wall of said suction tube, said lumen having an opening at the distal end thereof opening into said suction tube andan opening at the proximal end thereof external to said suction tube.

4. An assembly according to claim 2 wherein a second longitudinally extending lumen is provided in a wall of said suction tube spaced apart from said weakened portions, said lumen having an opening at the distal end thereof opening into said suction tube and an opening at the proximal end thereof external to said suction tube.

5. An assembly according to claim 1 wherein said means for connecting the lumen of said suction tube to a source of suction is in the form of a tubular body mounted at the proximal end of said suction tube, said body having one end adapted for fluid connection to the lumen of said suction tube and another end closed by a cap, said cap having an aperture therein adapted to receive said enteral feeding catheter in sliding sealing engagement, said body further including a branch pipe adapted for connection to a source of suction.

6. An assembly according to claim 5 wherein said means for connecting the lumen of said suction tube to a source of suction is in the form of a tubular body mounted at the proximal end of said suction tube, said body having one end adapted for fluid connection to the lumen of said suction tube and another end closed by a cap, said cap having an aperture therein adapted to receive said enteral feeding catheter in sliding sealing engagement, said body further including a branch pipe adapted for connection to a source of suction.

7. An assembly according to claim 1, wherein the lumen of said suction tube has an axial opening at the distal end thereof that is at least as large as the outside diameter of the portion of the catheter extending proximally thereof and wherein the distal end of said catheter adjustably extends beyond the distal end of said suction tube by slidable movement of said catheter relative to the distal end of said suction tube.

* * * * *